(12) United States Patent
Ries et al.

(10) Patent No.: US 9,079,014 B2
(45) Date of Patent: Jul. 14, 2015

(54) CONNECTOR MODULE ASSEMBLIES, METHODS, AND COMPONENTS FOR IMPLANTABLE MEDICAL ELECTRICAL DEVICES

(71) Applicant: Medtronic, Inc., Minneapolis, MN (US)

(72) Inventors: Andrew J. Ries, Lino Lakes, MN (US); Jeevan M. Prasannakumar, Circle Pines, MN (US); Richard P. Nelson, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 4 days.

(21) Appl. No.: 14/153,109

(22) Filed: Jan. 13, 2014

(65) Prior Publication Data
US 2014/0123490 A1 May 8, 2014

Related U.S. Application Data

(62) Division of application No. 13/473,934, filed on May 17, 2012, now Pat. No. 8,628,348.

(51) Int. Cl.
| | |
|---|---|
| *H01R 13/405* | (2006.01) |
| *A61N 1/05* | (2006.01) |
| *H01R 43/24* | (2006.01) |
| *A61N 1/375* | (2006.01) |
| *H01Q 1/27* | (2006.01) |
| *H01R 103/00* | (2006.01) |
| *H01R 4/02* | (2006.01) |
| *H01R 4/34* | (2006.01) |
| *H01R 24/58* | (2011.01) |

(52) U.S. Cl.
CPC ............... *A61N 1/05* (2013.01); *A61N 1/3752* (2013.01); *H01Q 1/273* (2013.01); *H01R 43/24* (2013.01); *H01R 4/023* (2013.01); *H01R 4/34* (2013.01); *H01R 24/58* (2013.01); *H01R 2103/00* (2013.01); *H01R 2201/12* (2013.01); *Y10T 29/49174* (2015.01); *Y10T 29/49204* (2015.01)

(58) Field of Classification Search
USPC .................. 439/736, 277, 909, 526, 814, 804; 607/37, 36; 411/377, 360, 393
See application file for complete search history.

(56) References Cited

U.S. PATENT DOCUMENTS

| | | | |
|---|---|---|---|
| 4,072,154 | A | 2/1978 | Anderson et al. |
| 4,316,471 | A | 2/1982 | Shipko et al. |
| 4,445,511 | A | 5/1984 | Cowdery et al. |
| 4,907,592 | A | 3/1990 | Harper |
| 4,932,409 | A | 6/1990 | Hirschberg |
| 5,509,928 | A | 4/1996 | Acken |
| 5,626,626 | A | 5/1997 | Carson |
| 5,679,026 | A | 10/1997 | Fain et al. |
| 5,989,077 | A * | 11/1999 | Mast et al. ............ 439/814 |
| 6,044,302 | A * | 3/2000 | Persuitti et al. ......... 607/37 |

(Continued)

*Primary Examiner* — Alexander Gilman
(74) *Attorney, Agent, or Firm* — Evans M. Mburu

(57) ABSTRACT

A contact component of an implantable medical device connector module assembly includes a threaded bore in fluid communication with a connector bore thereof, and a flanged bore in fluid communication with the threaded bore. A perimeter surface of the flanged bore creates a shutoff with a pin during injection molding to form an insulative body of the assembly, and a perimeter surface of an insulative bore formed around the pin is preferably flush with that of the flanged bore of the contact component. A centerline axis of the flanged bore is preferably aligned with that of the threaded bore, for example, so that the molded insulative bore has a centerline axis aligned with that of the threaded bore of the contact component.

7 Claims, 13 Drawing Sheets

(56) References Cited

U.S. PATENT DOCUMENTS

| | | |
|---|---|---|
| 6,205,358 B1 | 3/2001 | Haeg et al. |
| 6,817,905 B2 | 11/2004 | Zart et al. |
| 6,895,276 B2 | 5/2005 | Kast et al. |
| 7,133,722 B2 * | 11/2006 | Hansen et al. ............... 607/37 |
| 7,155,283 B2 | 12/2006 | Ries et al. |
| 7,308,313 B1 | 12/2007 | Lim et al. |
| 7,309,262 B2 | 12/2007 | Zart et al. |
| 7,317,946 B2 | 1/2008 | Twetan et al. |
| 7,472,505 B2 | 1/2009 | Zart et al. |
| 7,489,968 B1 | 2/2009 | Alexander et al. |
| 7,526,339 B2 | 4/2009 | Lahti et al. |
| 7,537,493 B2 | 5/2009 | Ries et al. |
| 7,711,429 B1 * | 5/2010 | Lim ............................ 607/37 |
| 7,717,754 B2 | 5/2010 | Ries et al. |
| 8,032,221 B2 * | 10/2011 | Wengreen et al. ........... 607/37 |
| 8,065,008 B2 | 11/2011 | Sommer et al. |
| 8,105,003 B2 * | 1/2012 | Fruland et al. ............... 411/377 |
| 8,914,110 B2 * | 12/2014 | He et al. ...................... 607/36 |
| 8,942,807 B2 * | 1/2015 | Edgell et al. ................. 607/37 |
| 8,945,451 B2 * | 2/2015 | Ries et al. .................... 264/272.14 |
| 2003/0040780 A1 * | 2/2003 | Haeg et al. ................... 607/36 |
| 2004/0093038 A1 | 5/2004 | Biggs et al. |
| 2004/0122481 A1 * | 6/2004 | Tidemand et al. ........... 607/37 |
| 2005/0131481 A1 | 6/2005 | Ries et al. |
| 2005/0131483 A1 | 6/2005 | Zhao et al. |
| 2006/0247716 A1 | 11/2006 | Fruland et al. |
| 2006/0259092 A1 | 11/2006 | Spadgenske et al. |
| 2007/0100386 A1 * | 5/2007 | Tronnes et al. .............. 607/37 |
| 2010/0285697 A1 | 11/2010 | Zart et al. |
| 2012/0123497 A1 * | 5/2012 | Sherva et al. ................ 607/36 |
| 2013/0307184 A1 * | 11/2013 | Ries et al. .................... 264/272.14 |
| 2013/0309889 A1 | 11/2013 | Ries et al. |

* cited by examiner

CONNECTOR MODULE ASSEMBLIES, METHODS, AND COMPONENTS FOR IMPLANTABLE MEDICAL ELECTRICAL DEVICES

CROSS-REFERENCE TO RELATED APPLICATION

The present application is a divisional of U.S. application Ser. No. 13/473,934, filed on May 17, 2012, now allowed. The application is also related to the co-pending and commonly-assigned United States Patent Application, filed concurrently herewith, and is entitled IMPLANTABLE MEDICAL ELECTRICAL DEVICE CONNECTOR MODULE ASSEMBLIES AND METHODS.

FIELD OF THE DISCLOSURE

The present invention pertains to implantable medical devices, and, more particularly to connector module assemblies thereof.

BACKGROUND

Implantable medical systems that are designed to deliver electrical stimulation, for example, to cardiac muscle or the spinal cord, and/or to monitor bodily electrical activity, typically include a relatively compact implantable device, for example, like an exemplary device 100 shown in FIG. 1, and one or more elongate implantable electrical leads (not shown). With reference to FIG. 1, those skilled in the art will appreciate that three connector terminals of one or more leads may be plugged into bores 121, 122 of a connector module assembly 115 of device 100, to electrically couple electrodes of the one or more leads to a power source and circuitry which is contained in a hermetically sealed housing 104, for example, formed from a Titanium alloy, on which connector module assembly 115 is mounted. Connector module assembly 115 includes one or more contact surfaces exposed along a length of each bore 121, 122 for electrical coupling with corresponding contact surfaces of the corresponding lead connector terminal inserted therein. An insulative body of connector module assembly 115 supports and isolates the contact components and corresponding conductive interconnects that extend from the contact components to hermetically sealed feedthroughs, within the insulative body, for electrical coupling of the contact components to the circuitry and power supply within housing 104. Numerous constructions and assembly methods for implantable medical device connector module assemblies are known in the art, some of which are disclosed in commonly assigned U.S. Pat. Nos. 6,895,276, 7,309,262, 7,317,946, 7,526,339, 7,717,754 and 8,032,221. However, there is still a need for new and improved connector module assembly constructions and associated assembly methods.

SUMMARY

A contact component of an implantable medical device connector module assembly, according to some embodiments of the present invention, includes a connector bore, which is aligned and in fluid communication with a corresponding connector bore of an insulative body of the assembly (i.e. to receive insertion of a connector terminal of an implantable medical electrical lead therein), and a threaded bore, which is adapted to mate with a set screw and position a conductive end thereof in contact with a connector terminal inserted within the connector bore. According to some preferred embodiments, the contact component further includes a flanged bore, which is in fluid communication with the threaded bore; and the insulative body preferably includes an insulative bore that extends from the flanged bore of the contact component to an opening, at a surface of the body, for example, to form either a bond zone for a sealing grommet/septum, or a sealing zone for a seal member of a sealing type of set screw that is engaged within the threaded bore.

The flanged bore of each contact component, according to some preferred embodiments and methods, has a relatively smooth perimeter surface sized to create a shutoff with a pin when the flanged bore is positioned thereabout during injection molding to form the insulative body of the connector module assembly. A perimeter surface of an insulative bore of the body, formed around the pin, is preferably flush with the flanged bore. Furthermore, a centerline axis of the flanged bore is preferably aligned with that of the threaded bore, for example, to within approximately 0.002 inch (0.05 mm), so that the resulting insulative bore of the molded body has a centerline aligned with that of the threaded bore.

According to some embodiments and methods, in which an elongate finger-like portion of an electrical component is welded to each contact component of the connector module assembly, prior to molding, a welding fixture pin may be inserted within the above-described flanged bore of each contact component, such that the engagement therebetween is similar to that with the aforementioned pin used in molding, in order to hold each contact component in position, for example, relative to one another, for welding. According to those preferred embodiments that include a plurality of the above-described contact components, the fit of each welding fixture pin and of each mold core pin in the flanged bore of the corresponding contact component can be useful for holding a desired positional tolerance of the contact components relative to one another during welding and molding.

According to some methods, a two-stage molding process is employed to form the insulative body of the connector module assembly, such that the insulative body includes a core portion, formed by a first shot of insulative material, and an overlay portion, formed by a second shot of insulative material. At least one of the above-described contact components may be molded within the core portion during the first stage of the molding process; and the above-described insulative bore, which extends from the flanged bore of each contact component, is preferably wholly formed by the second shot of insulative material.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 1:
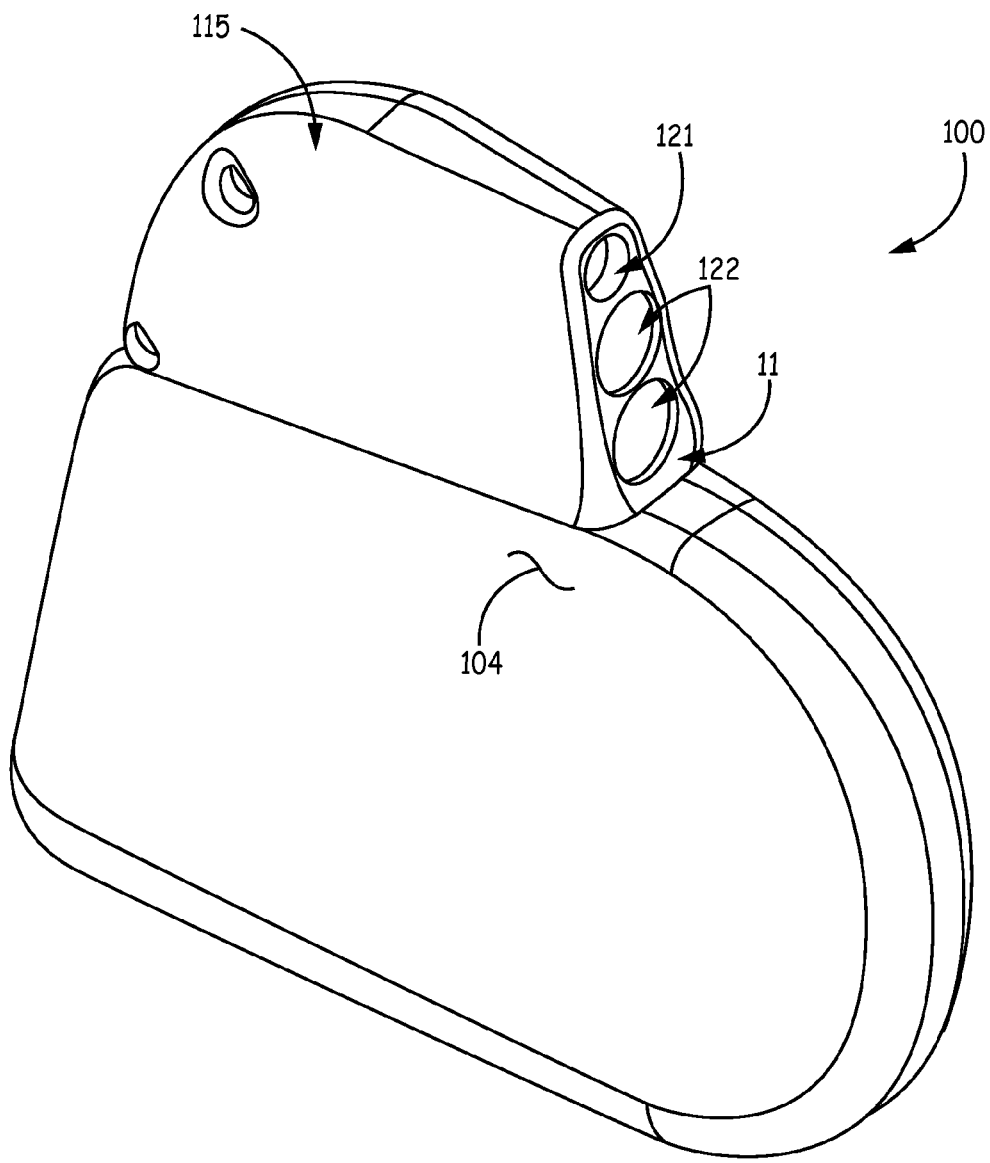
FIG. 1 is a perspective view of an exemplary implantable medical device including a connector module assembly, which may be constructed according to some embodiments and methods of the present invention.
Figure 2A:
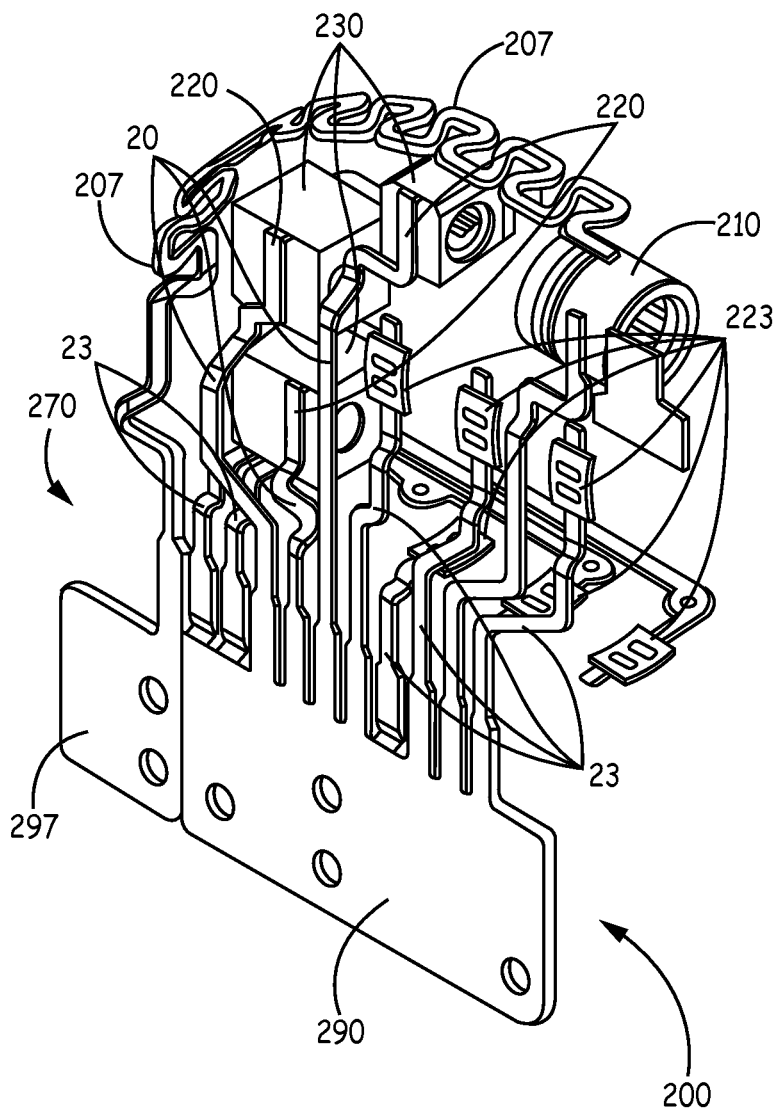
FIG. 2A is a perspective view of a welded assembly of components, according to some embodiments and methods.
Figures 2B, 2C:
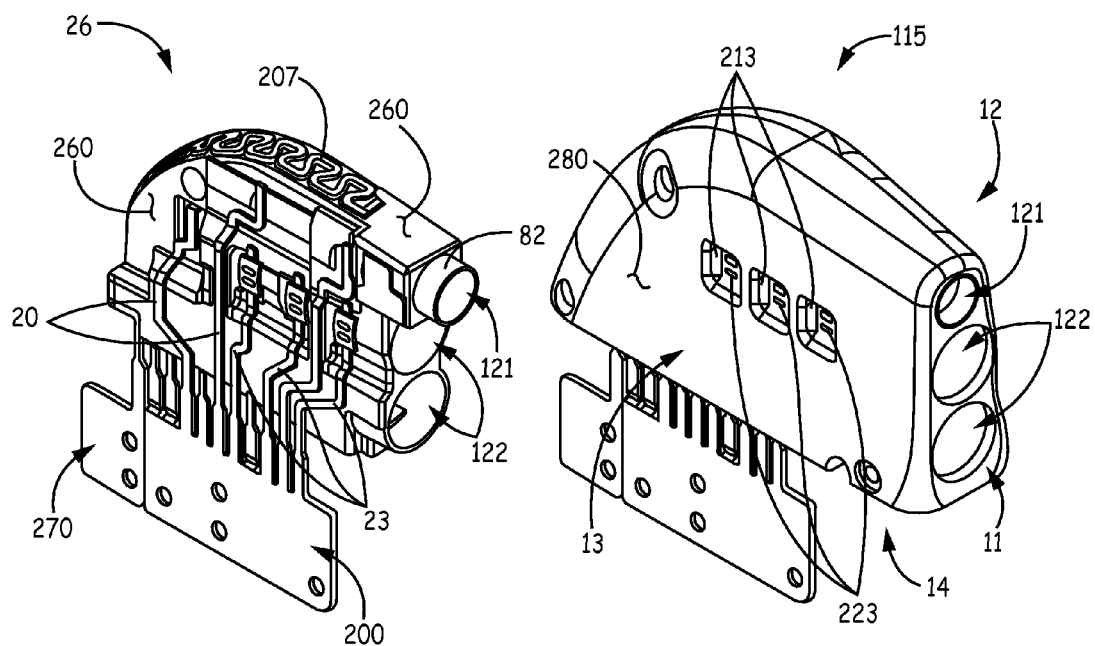
FIGS. 2B-C are perspective views of molded assemblies for a connector module assembly, according to some methods and embodiments.

FIG. 1 is a perspective view of implantable medical device 100 including connector module assembly 115, which may be constructed according to some embodiments and methods of the present invention, for example, as introduced by FIGS. 2A-C. According to some embodiments, connector module assembly 115 includes two types of connector bores, wherein connector bore 121 corresponds to a first type of bore and each of connector bores 122 corresponds to a second type; an indicator or marker may be included in the construction of connector module assembly 115, according to some methods described below, to identify bore 121 as the first type. As mentioned above, each of bores 121, 122 is configured to receive a connector terminal of an implantable medical electrical lead for electrical coupling of the lead to the power source and circuitry contained in housing 104.

FIG. 2A is a perspective view of a welded assembly that includes electrical components 200, 270, set screw block (ssb) contact components 230, and a multi-beam contact (mbc) component 210. FIG. 2A illustrates each electrical component 200, 270 including a feedthrough interface panel portion 290, 297 and one or more elongate finger-like portions 20, 23, 207 extending therefrom; wherein each elongate finger-like portion 20, 23 of electrical component 200 includes a contact interface 220, 223 coupled to a corresponding conductive trace (not shown) formed on interface panel portion 290; and wherein elongate finger-like portion 207 of component 270 forms an antenna. Antenna 207 is useful for telemetry communications known in the art, for example, as described in the above-referenced commonly assigned U.S. Pat. No. 7,317,946. FIG. 2A further illustrates each contact interface 220 coupled to a corresponding ssb contact component 230 or to mbc component 210, and each contact interface 223 not yet coupled to a corresponding contact component that will be described below. Those skilled in the art will appreciate that each contact component of connector module assembly 115 has a connector bore, aligned with the corresponding bore 121, 122, within which electrical contact is made with a corresponding contact element on an inserted lead connector terminal. Each feedthrough interface panel portion 290, 270 is adapted for mounting to a sidewall of device housing 104 (FIG. 1) and for coupling to the aforementioned hermetically sealed feedthrough assembly (not shown), which may be constructed according to embodiments and methods known in the art.

According to some methods of the present invention, which will be described in greater detail below, an insulative body of connector module assembly 115 is molded around the welded assembly of FIG. 2A, preferably in two shots, or stages, for example, as illustrated in FIGS. 2B-C. FIG. 2B illustrates a core assembly 26 including a first shot of an insulative material, that forms a core portion 260 to partially surround and capture the welded assembly. The insulative material is preferably a medical grade thermoplastic material, such as polyurethane, for example, having a durometer of between approximately 50 and 90 on a shore D scale. With reference to FIG. 2B, a side of each elongate finger-like portion 20, 23, 207 is exposed, while core portion 260 extends over an opposite side of each, to capture each portion 20, 23, 207 in relatively rigid relation thereto. It should be noted that, according to some alternate methods, any or all of electrical component 200, ssb contact components 230 and mbc contact component 210 may be integrated, or assembled into core assembly 26 after core portion 260 is formed around electrical component 270 to capture antenna 207 in relatively rigid relation thereto. FIG. 2C illustrates an overlay portion 280 formed by a second shot of insulative material, for example, the same thermoplastic material that forms core portion 260, that has been molded around core assembly 26 to form an outer surface of the insulative body of connector module assembly 115; the outer surface may have first, second, third and fourth faces 11, 12, 13, 14, as designated in FIG. 2C.

According to the illustrated embodiment, overlay portion 280 extends over the sides of finger-like portions 20, 23, 207 that were exposed in core assembly 26, yet, FIG. 2C illustrates each of a first set of contact interfaces 223 exposed through apertures 213 that are formed through third face 13 of overlay portion 280 of the insulative body, and, with reference to FIG. 2A, it should be understood that a second set of contact interfaces 223 are exposed through similar apertures formed through fourth face 14. According to the illustrated embodiment, a stack of contact components is inserted within each one of the lower two bores 122, such that a connector bore of each stack is approximately coaxial with the corresponding bore 122, for receipt of a corresponding medical electrical lead terminal therein, and each contact component of the stack is aligned with a corresponding contact interface 223 for coupling thereto, for example, by laser welding, through a corresponding aperture 213, after which, each aperture 213 is sealed off with an insulative adhesive, for example, silicone medical adhesive. Connector module constructions including such stacks of contact components are described in commonly assigned U.S. Pat. Nos. 6,895,276 and 7,717,754, which are hereby incorporated by reference. With further reference to FIGS. 2A-C, each of the stack contact components, ssb contact components 230 and mbc component 210 include a connector bore, which is aligned and in fluid communication with the corresponding bore 121, 122, and each component connector bore has a corresponding contact surface for electrical coupling with a contact surface of a corresponding medical electrical lead connector terminal that is received therein.

Figure 3:
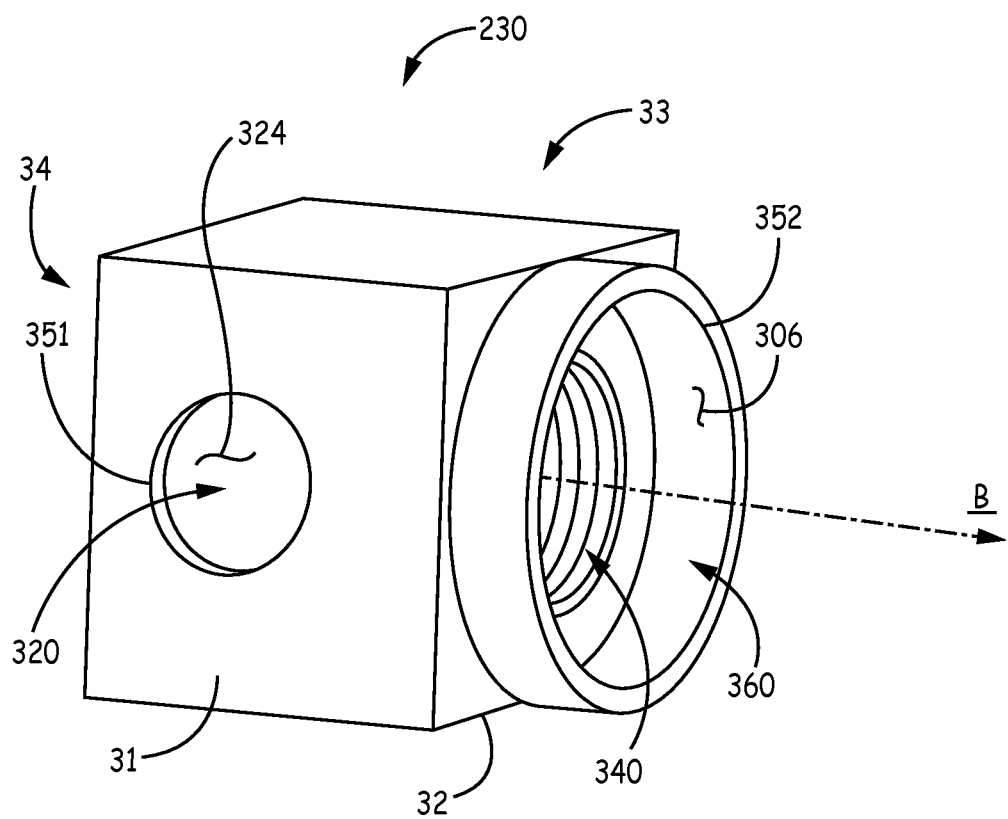
FIG. 3 is a perspective view of a contact component, according to some embodiments of the present invention.

FIG. 3 is a perspective view of one of ssb contact components 230, according to some embodiments of the present invention. FIG. 3 illustrates component 230 including a connector bore 320 and a threaded bore 340; connector bore 320 extends from an opening 351 at a first face 31 thereof and has an interior contact surface 324, and threaded bore 340 extends outward from connector bore 320 toward a second face 32 of component 230. Connector bore 320 preferably extends to another opening at a third face 33 of component 230, which is opposite first face 31. Threaded bore 340 is adapted to mate with a set screw so that a conductive end of the mating set screw is positioned within connector bore 320, for example, like a conductive end 505 of a set screw 500 shown in FIG. 5, which, when engaged as illustrated, forces an inserted lead connector terminal 50 into contact with contact surface 324.

FIG. 3 further illustrates a flanged bore 360 of ssb contact component 230 in fluid communication with threaded bore 340 and extending out from second face 32 to an opening 352. According to preferred embodiments of the present invention, flanged bore 360 has a relatively smooth perimeter surface 306 sized for a minimum slip-fit clearance fit around a mold pin, to provide a shutoff therewith that prevents the insulative material from flowing into the threads of threaded bore 340, during a molding process to form the insulative body of the connector module assembly. Creating such a shutoff, between a perimeter surface of flanged bore 360 and the mold pin, is an improvement over the prior art, in which mold pins are configured to mate with the threaded bore of ssb-type contact components, and/or a particular alignment and pressure of a terminal face of the mold pin, against an internal shoulder of the contact component, is critical to provide the necessary shutoff. Thus, it may be appreciated that the above-described flanged bore 360 of contact component 230 eliminates more time consuming and tedious processes that require threaded engagement with a mold pin and/or a repeatable alignment and pressure to provide shutoff during molding. Furthermore, prior art pins that engage with the threads of contact components can make these threads more vulnerable to damage during processing.

Figure 4A:
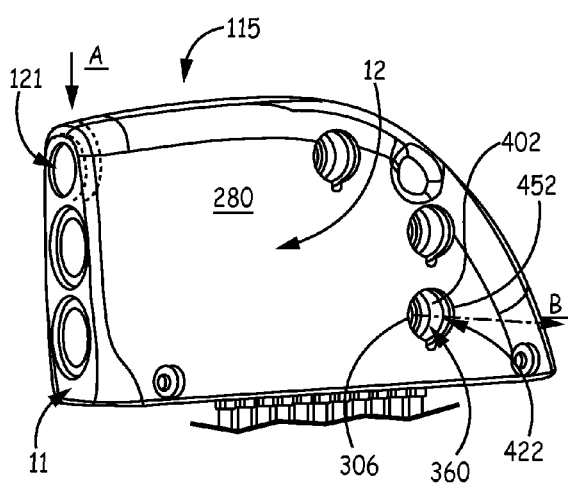
FIG. 4A is a perspective view of a connector module assembly, according to some embodiments.
Figure 4B:
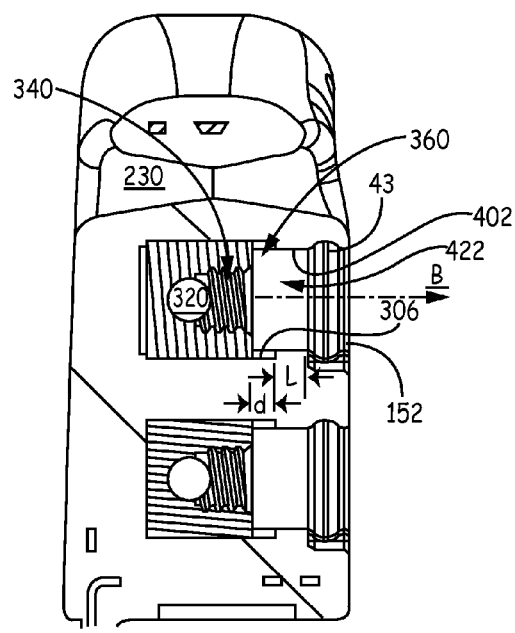
FIG. 4B is a section view along centerline B of FIG. 4A, according to some embodiments.
Figure 5:
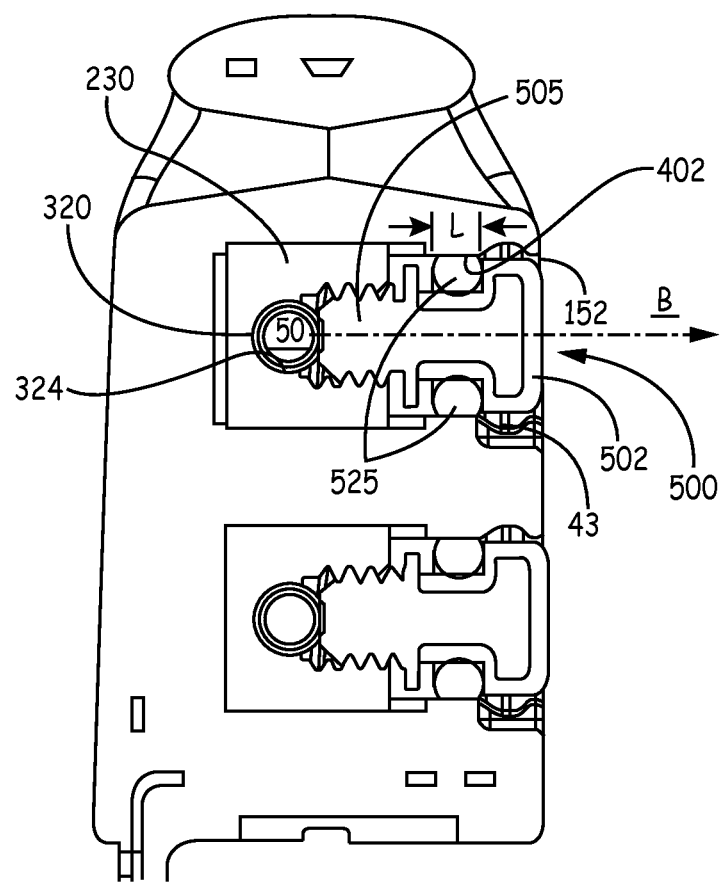
FIG. 5 is a section view, similar to that shown in FIG. 4B, wherein sealing set screws are mated with contact components, according to some embodiments.

According to some preferred embodiments, a centerline axis of flanged bore 360 is aligned with a centerline axis B of threaded bore 340, for example, to within approximately 0.002 inch (0.05 mm), so that, in addition to creating the shutoff, flanged bore 360 locates an engaged mold pin to form an insulative bore thereabout that has a centerline axis aligned with axis B, for example, to within approximately 0.002 inch (0.05 mm). With reference to FIGS. 4A-B, such an insulative bore 422 is shown extending from flanged bore 360 of component 230, outward to an opening 152 on a second face 12 of connector module assembly 115. FIGS. 4A-B illustrate insulative bore 422 having a perimeter surface 402 that is flush with perimeter surface 306 of flanged bore 360. With reference to FIG. 5, the preferred alignment of insulative bore 422 is advantageous if perimeter surface 402 of insulative bore 422 forms a sealing zone for a seal member 525 (i.e. silicone O-ring) of set screw 500, when set screw 500 is engaged within threaded bore 340 and conductive end 505 is positioned within connector bore 320 to force inserted lead terminal 50 into contact with conductive surface 324. FIG. 5 further illustrates an insulative jacket 502 surrounding a head and neck of set screw 500, and the above-referenced commonly assigned U.S. Pat. No. 8,032,221 describes embodiments of sealing set screws similar to set screw 500.

FIGS. 4B and 5 further illustrate insulative bore including an optional groove 43 formed therein, in proximity to opening 152. According to the illustrated embodiment, optional groove 43 is sized to receive seal member 525, in a relaxed state, when set screw 500 is retracted up through opening 152 and out of connector bore 320, and, thereby, retains set screw 500, prior to positioning conductive end 505 within connector bore 320. According to an exemplary embodiment, a length L of that portion of insulative bore 422, which forms the sealing zone between optional groove 43 and flanged bore 360 of ssb contact component 230, is between approximately 0.03 inch (0.76 mm) and approximately 0.05 inch (1.27 mm), preferably approximately 0.04 inch (1 mm). Flanged bore 360 may have a depth d of between approximately 0.010 inch (0.25 mm) and approximately 0.04 inch (1 mm), wherein the lower end of depth d is limited by the above-described shutoff function, and the upper end of depth d is limited by size constraints on connector module assembly 115, for example, such that insulative bore 422 has an adequate length for the sealing zone and optional groove 43. It should be noted that, according to alternate embodiments, in lieu of the sealing zone, formed by perimeter surface 402, and optional groove 43, insulative bore 422 forms a bonding zone for a sealing grommet, or septum, for use in conjunction with a standard set screw, according to constructions and methods known in the art. In this case, depth d of flanged bore 360 of component 230 may extend up to approximately 0.06 inch (1.5 mm), since insulative bore 422 need not accommodate the above-described sealing zone and optional groove 43. Insulative bore 422 is preferably entirely formed by a single shot of insulative material, for example, by the above described second shot, to prevent the potential formation of discontinuities along the inner surface of bore 422, for example, at an interface between core portion 260 and overlay portion 280, but may, according to alternate methods, be formed in two portions, for example, by the above-described first and second shots.

Figure 6A:
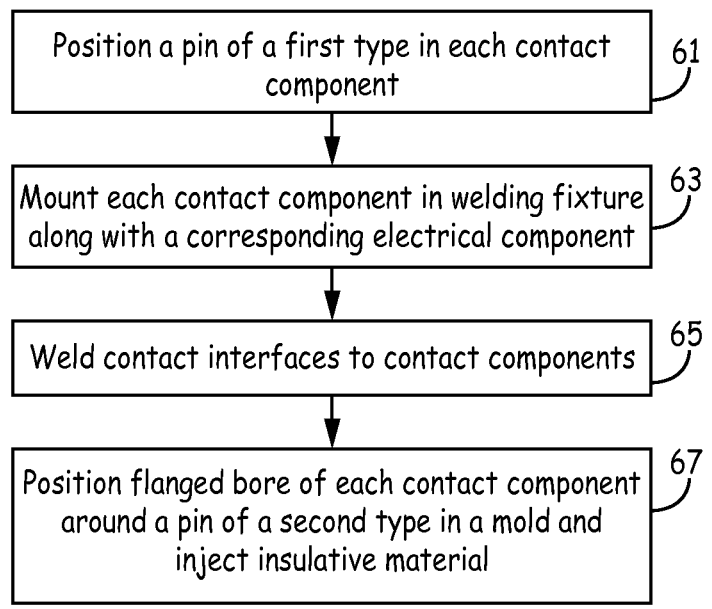
FIG. 6A is a flow chart outlining some methods of the present invention.

FIG. 6A is a flow chart outlining some methods of the present invention, with focus on the above-described ssb contact components 230. In an initial step 61, a pin of a first type is positioned in each ssb contact component 230. For example, with reference to FIG. 7A, each of pins 71, 711 is a first type of pin, or core pin, positioned within the connector bore of the corresponding ssb contact component 230, such that a shoulder 713 of each core pin 71, 711 abuts first face 31 (FIG. 3) of the corresponding component 230, and a tip of each pin 71, 711 extends out through the opening of the corresponding connector bore 320 at the corresponding third face 33. Next, per step 63, each contact component 230, with the first type of pin inserted therein, is mounted in a welding fixture, for example, along with components shown in FIG. 2A, in particular, a corresponding electrical component having contact interfaces (i.e. component 200 with interfaces 220) that are subsequently coupled to contact components 230, for example, by laser welding, according to methods known in the art, per step 65.

Figure 7A:
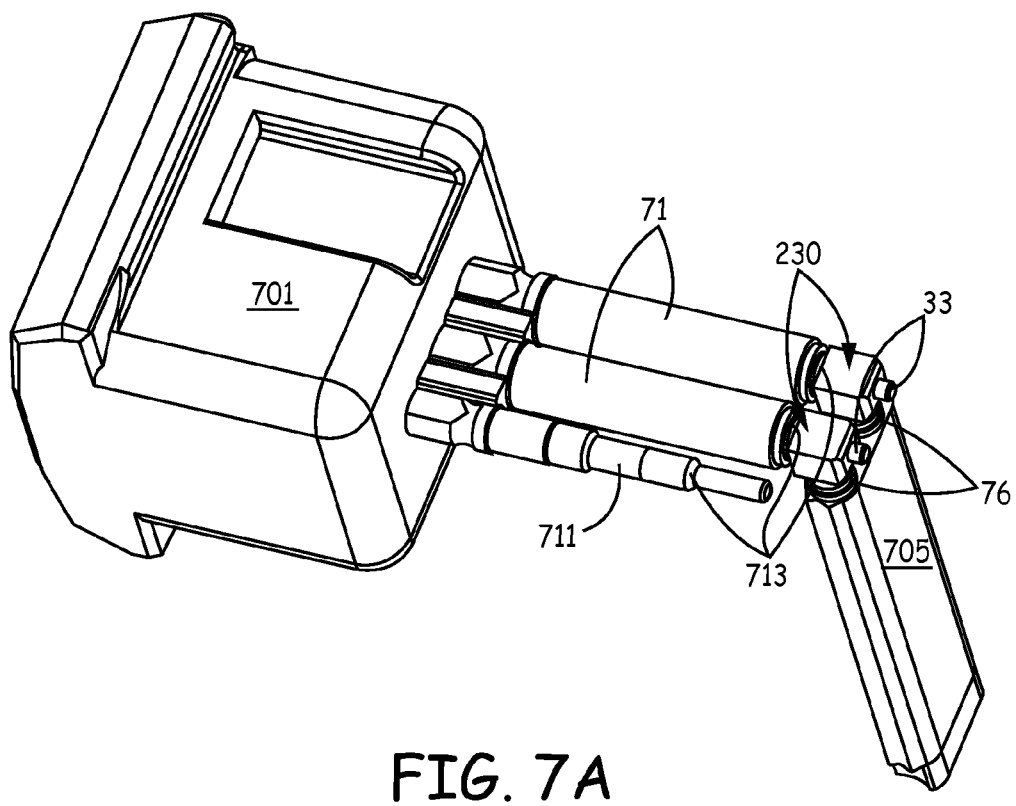
FIG. 7A is a perspective view of contact components engaged with two types of pins, according to some methods of the present invention.

According to some preferred methods, mounting each contact component 230 involves securing each inserted pin of the first type to the fixture, for example, by a holding structure 701 shown in FIG. 7A, and positioning flanged bore 260 of each ssb contact component 230 around a corresponding welding fixture pin, each of which is also secured to the fixture. For example, FIG. 7A shows flange bore 260 of each component 230 positioned around a corresponding welding fixture pin 76, each of which is supported by a block 705 that provides an interface for securing pins 76 to the welding fixture. Thus, ssb contact components 230 are held in place, with respect to one another by pins 71, 76, while contact interfaces 220 of electrical component 200 (FIG. 2A) are positioned and welded to each contact component, per step 65. Although not shown in FIG. 7A, it should be understood that the welding fixture may include a cradle or support structure, for example, similar to that shown for mold tooling in FIG. 7B, in order to provide extra support for retaining all the components and pins in position, relative to one another, during welding, with a desired positional tolerance.

According to step 67 of FIG. 6A, when the welded assembly of ssb contact components 230 and electrical component 200 are placed in a mold, a flanged bore of each contact component, for example, flanged bore 360 (FIG. 3), is positioned around a pin of a second type, prior to injecting insulative material to form the insulative body. According to preferred embodiments and methods, as described above, perimeter surface 306 of each flanged bore 360 is a minimum slip-fit clearance fit around the corresponding mold pin in order to create a shutoff, for example, wherein the mold pin extends at least approximately 0.01 inch (0.025 mm) into flanged bore 360. It should be noted that, in step 63, perimeter surface 306 of flanged bore 360 of each component 230 may also be a minimum slip-fit clearance fit around the corresponding welding fixture pin, for example, to hold a desired positional tolerance of contact components 230 relative to one another during welding. Although, according to some methods, the insulative body of connector module assembly 115 may be wholly formed by a single shot of insulative material, per step 67, some preferred methods, as introduced above, employ a two stage molding process, alternatives of which are described in greater detail in conjunction with FIGS. 6B, 7B-D and 8.

Figure 6B:
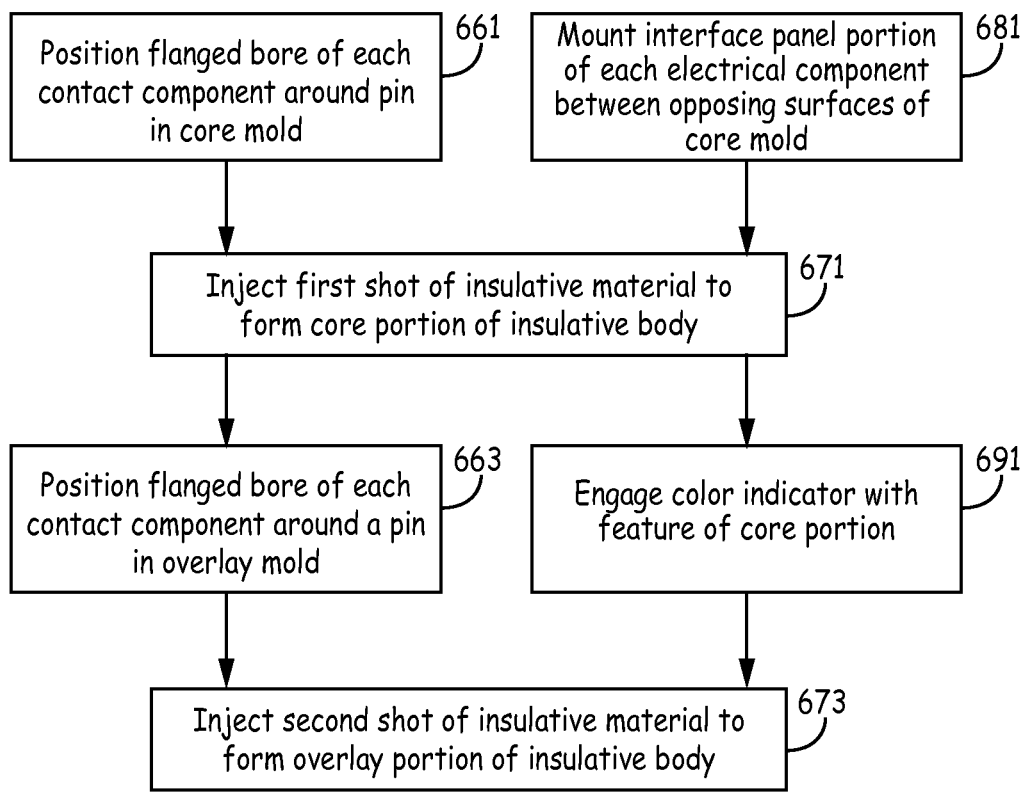
FIG. 6B is a flow chart outlining some additional methods.
Figure 7B:
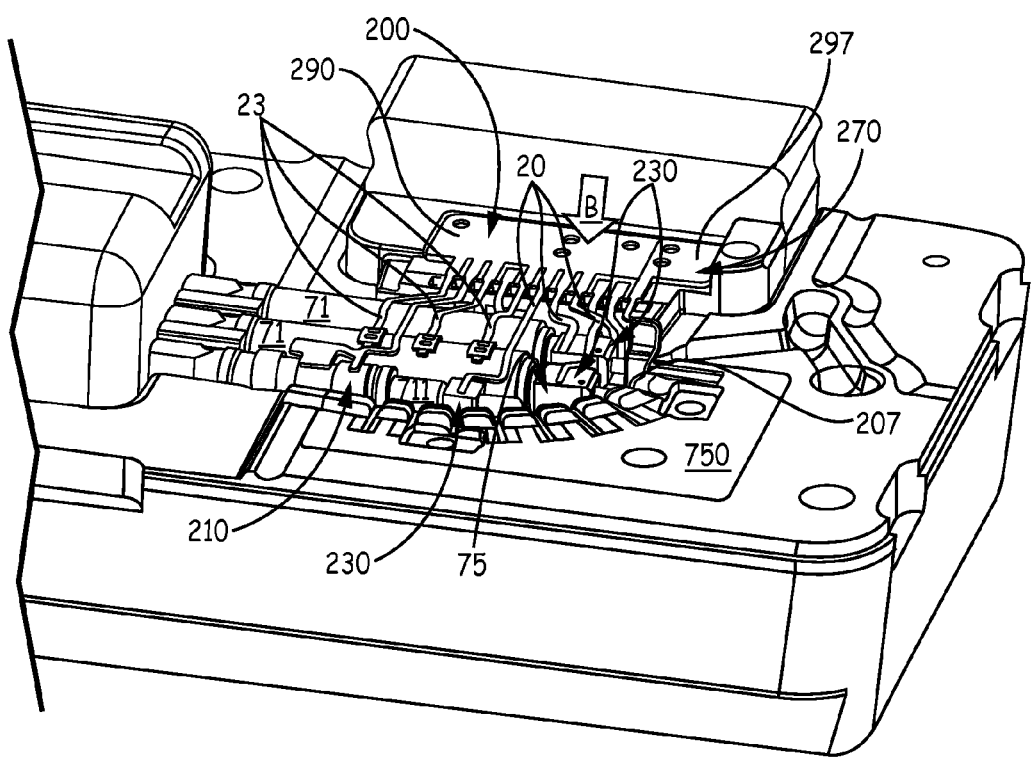
FIG. 7B is a perspective view of a portion of mold tooling in which the welded assembly of components are placed for molding a core portion of an insulative body of a connector module assembly, according to some embodiments and methods.
Figure 7C:
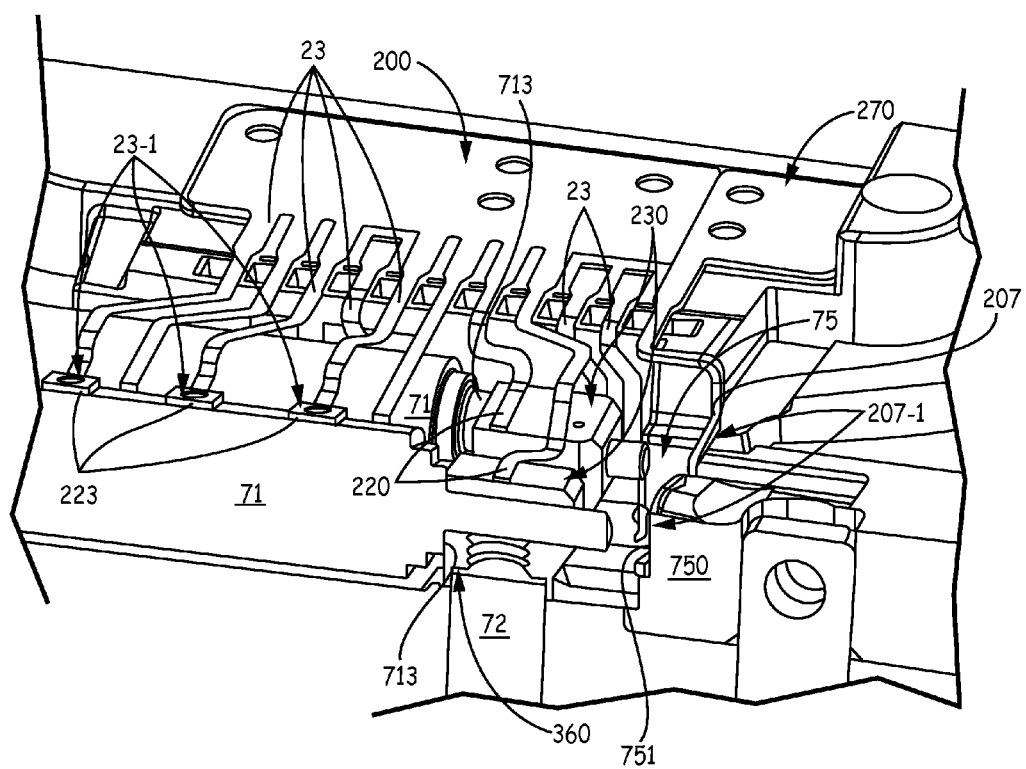
FIG. 7C is another perspective view, with cross-section, of the placed components and portion of the mold tooling shown in FIG. 7B.

According to steps 661 and 681 of FIG. 6B, and with reference to FIGS. 7B-C, each contact component, for example, ssb contact components 230, and each electrical component, for example, components 200 and 270, are positioned in a core mold 750 for a first stage of molding that forms core portion 260 of the connector module insulative body, per step 671. With reference to FIGS. 7B-C, it should be noted that core pins 71, 711 of the first type, which were previously positioned for welding, per step 65 described above, remain positioned within the connector bores of the contact components in mold 750 for the formation of insulative connector bores in the first stage of molding. However, according to alternate methods, different core pins may be inserted into contact component connector bores for molding. FIG. 7B illustrates feedthrough interface panel portion 290, 297 of each electrical component 200, 270 placed against a first surface of core mold 750, and an arrow B indicating the direction in which a second surface of a second part (not shown) of core mold 750 will face, when positioned against panel portions 290, 297, to mount portions 290, 297 between the two surfaces, per step 681.

Figure 7D:
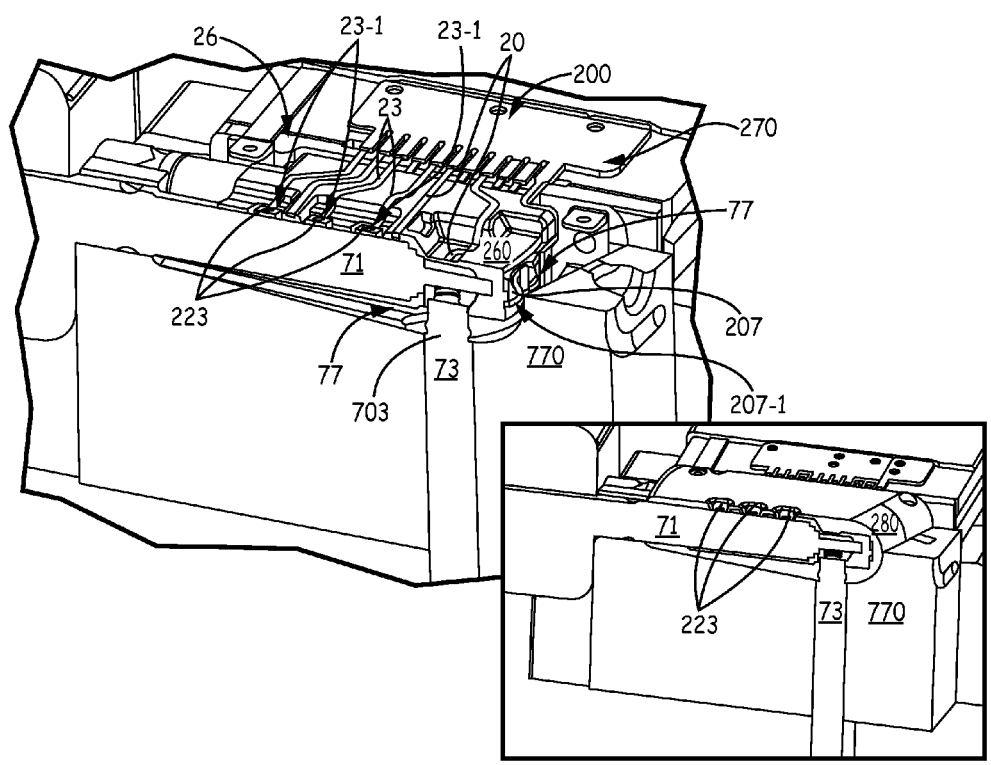
FIG. 7D shows two perspective views, with cross-sections, of a core assembly placed in an overlay mold, according to some embodiments and methods.

FIG. 7B further illustrates elongate finger-like portions 23, 20 of electrical component 200 and elongate finger-like portion/antenna 207 of component 270 extending into a cavity 75 of mold 750 such that a first side of each touches another side of mold 750. With reference to FIG. 7C, a surface 751 of mold 750 is indicated, along with a first side 207-1 of antenna 207 that touches surface 751. Furthermore, a first side 23-1 of several of elongate finger-like portions 23 is indicated, and it should be understood that another surface of the second part of mold 750, which is not shown, will touch sides 23-1, when the second part is moved into place, for example, per arrow B of FIG. 7B. With reference to FIG. 7D, it can be seen that first side 207-1 of antenna 207, after core portion 260 is formed, will be exposed in a cavity 77 of an overlay mold 770.

Figure 8:
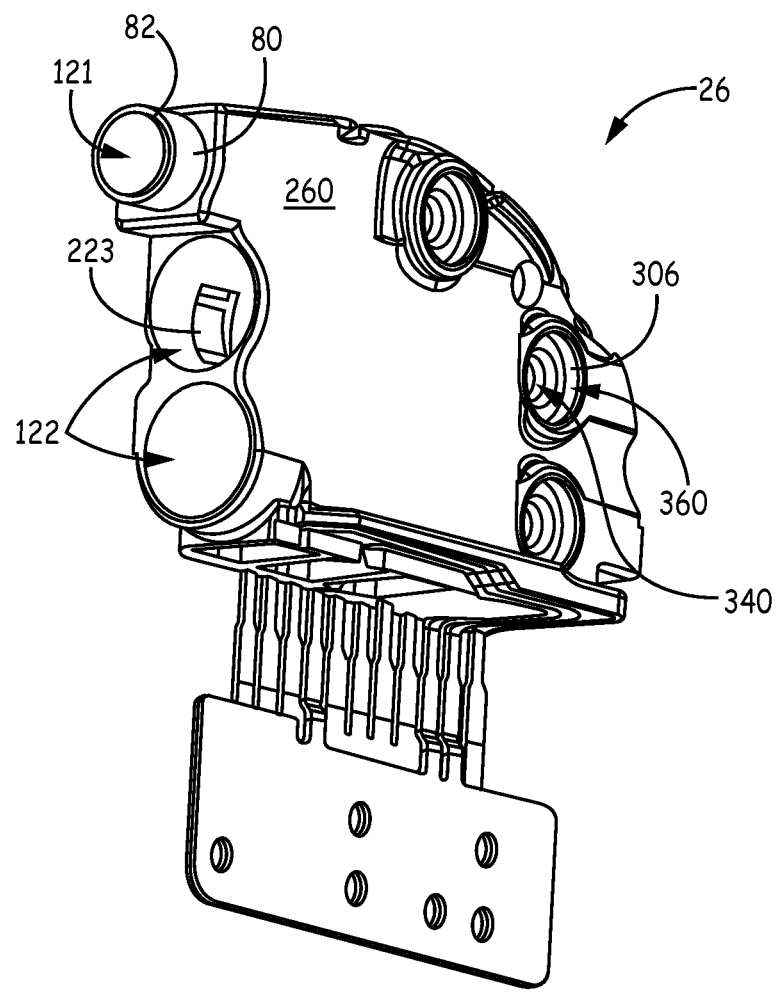
FIG. 8 is a perspective view of a core assembly, according to some embodiments and methods.

FIG. 7C further illustrates the first set of contact interfaces 223 of finger-like portions 23 touching a surface of pin 71 in mold cavity 75, and, with reference back to FIG. 2A, it should be understood that the second set of contact interfaces 223 are touching a surface of the other pin 71 which cannot be seen in FIG. 7C. According to the above-described embodiments, following molding and the removal of core pins 71, contact interfaces 223 are exposed within the insulative connector bores formed around pins 71, for example, as can be seen in FIG. 8, so that contact components, which are subsequently inserted into the bores 212, can be coupled to interfaces 223. With further reference to FIG. 7C, flanged bore 360 of one of ssb contact components 230 can be seen positioned around a pin 72, per step 661, for example, so that pin 72 extends at least approximately 0.01 inch (0.25 mm) into flanged bore 360. According to some preferred embodiments and methods, as described above, perimeter surface 306 of flanged bore 360 of each ssb contact component 23 that is placed in mold 750 is a minimum slip-fit clearance fit around the corresponding pin 72 to create a shutoff for the subsequent injection of the first shot of insulative material, per step 671.

The first shot of insulative material, for example, which forms core portion 260 of the insulative body of connector module assembly 115 (FIGS. 2B and 8), is preferably a medical grade polyurethane (i.e. Lubrizol Thermedics™ Tecothane™ or Pellethane®) having a durometer of approximately 75 on a shore D scale. With further reference to FIG. 8, in conjunction with FIG. 3, an outer surface of core portion 260, in proximity to each flanged bore 360 of the corresponding component 230, is preferably approximately flush with opening 352 of flanged bore 360. FIG. 8 further illustrates core portion 260 of the insulative body having been formed with a flange feature 82 that extends about a perimeter of connector bore 121; feature 82 may also be seen in FIG. 2B. As described above, when connector bore 121 corresponds to a first type that is different from bores 122, a color indicator 80 may be engaged with feature 82, according to an optional step 691 of FIG. 6B, to distinguish bore 121 from the other bores 122 of the second type. According to embodiments that include indicator 80, overlay portion 280, which is formed per step 673, is translucent for viewing indicator 80 therethrough. According to an exemplary embodiment of connector module assembly 115, connector bore 121 conforms to the IS-1 industry standard, while connector bores 122 conform to the IS-4 industry standard, both of which standards are known to those skilled in the art of implantable medical electrical devices.

According to the illustrated embodiment, optional indicator 80 is formed as a ring, from either a biocompatible polymer or metal, which is mounted around feature 82, yet, according to some alternate embodiments and methods, optional indicator 80 may be a biocompatible ink, dye or paint applied to a surface of feature 82. With reference back to FIG. 4A, dashed lines represent an indicator, such as indicator 80, which is embedded in the insulative body of connector module assembly, for example, between core portion 260 and overlay portion 280. According to additional alternate embodiments, in lieu of flange feature 82, core portion 260 may include a recessed feature formed in proximity to bore 121, for example, a groove extending all or partway around the perimeter of bore 121, that is adapted to receive engagement of an optional color indicator similar to any embodiment described above for indicator 80. For any type of indicator, the indicator is preferably engaged with a feature of core portion 260 so that the indicator can be viewed from an angle that is approximately perpendicular to a longitudinal axis of bore 121, for example, as indicated by arrow A in FIG. 4A, although this need not be the case in every connector module assembly embodiment. The described two-shot molding method is particularly useful for incorporating a color indicator, such as indicator 80, in a connector module assembly, so, according to some alternate embodiments and methods, step 681, as well as steps 661 and 663, may be omitted.

With reference back to FIGS. 6B and 7B, core assembly 26 which is formed by the first shot of insulative material and the components shown in FIG. 7B, for example, per steps 661, 681, 671, may then be positioned, with optional indicator 80, in overlay mold 770, for example as illustrated in FIG. 7D. Again, each core pin 71, 711 may still remain positioned within the connector bores of the contact components in overlay mold 770. FIG. 7D illustrates elongate finger-like portions 20, 23 of component 200 and elongate finger-like portion/antenna 207 of component 270 being captured in rigid relation to core portion 260 of the insulative body, and having sides exposed in cavity 77 of mold 770 so that the second shot of injected insulative material will form overlay portion 280 of the insulative body, per step 673, over all or a portion of the exposed sides, for example, as shown in the boxed area of FIG. 7D. It should be noted, that, like for core mold 750 shown in FIG. 7B, a second part of overlay mold 770 is not shown in FIG. 7D, and that surfaces of the second part of overlay mold 770 will touch first sides 23-1 of elongate finger-like portions 23 in the area of contact interfaces 223 in order to form apertures 213 in overlay portion 280, according to the embodiment described above, in conjunction with FIG. 2C, and shown again in the boxed area of FIG. 7D. The described two-shot molding method is particularly useful to maintain control over the placement of elongate and relatively flexible parts, such as an entirety of antenna 207, relative to other components in a connector module assembly; so, according to some alternate embodiments and methods, step 691, as well as steps 661 and 663, may be omitted.

According to step 663, positioning core assembly 26 in mold 770 again involves positioning flanged bore 360 of each ssb contact component 23 around a pin in overlay mold 770, for example, a pin 73 of a third type shown in cross-section in FIG. 7D, wherein each pin 73 extends approximately 0.01 inch into the corresponding flanged bore 360, and each flanged bore 360 is a minimum slip-fit clearance fit around the corresponding pin 73 to create a shutoff for the subsequent second shot injection of insulative material, per step 673. FIG. 7D illustrates a length of pin 73 exposed within mold cavity 77 to allow an insulative bore, for example, insulative bore 422 shown in FIGS. 4A-B, to be formed in overlay portion 280, by the second shot of insulative material. FIG. 7D further illustrates an optional protrusion 703 along a profile of pin 73, which forms the above-described optional groove 43 in insulative bore 422, which can be seen in FIGS. 4B and 5. When this two-stage molding process is employed, insulative bore 422 is preferably entirely formed by the second shot of insulative material, to prevent the potential formation of discontinuities along the inner surface of bore 422, that may arise at an interface between core portion 260 and overlay portion 280. The second shot of insulative material is preferably a medical grade polyurethane (i.e. Lubrizol Thermedics™ Tecothane™ or Pellethane®) having a durometer of approximately 75 on a shore D scale.

Although molding in two stages may be preferred for forming connector module assemblies, like assembly 115, that include antenna 207 and/or color indicator 80, as described above, alternate methods can employ a single shot molding operation to form an insulative body of a connector module assembly that includes ssb contact components 230, which insulative body includes the above-described connector bores 121, 122 and insulative bores 422. In either case, the engagement of flanged bore 360 of each ssb contact component 230 with the corresponding mold pin allows each insulative bore 422 to be formed in alignment with threaded bore 340 of the corresponding component 230, and prevents the flow of plastic into the threads of the corresponding threaded bore 340 in an improved fashion over the aforementioned prior art methods that employ more time consuming and tedious processes to engage threads and/or make critical alignment, with sufficient pressure, to provide shutoff during molding In the foregoing detailed description, the invention has been described with reference to specific embodiments. However, it may be appreciated that various modifications and changes can be made without departing from the scope of the invention as set forth in the appended claims.

The invention claimed is:

1. A method for forming a connector module assembly for an implantable medical device, the method comprising:
   positioning a first pin in a connector bore of a contact component;
   positioning a flanged bore of the contact component around a second pin in a mold, the flanged bore being in fluid communication with the connector bore, and a perimeter surface of the positioned flanged bore being a minimum slip-fit clearance fit around the second pin to create a shutoff; and
   forming an insulative body of the connector module assembly by injecting an insulative material around the contact component and the first and second pins in the mold, the insulative body including an opening formed around the second pin and located at an outer surface of the insulative body, for passage into the flanged bore of the contact component.

2. The method of claim 1, wherein the insulative body further includes an insulative bore that extends from the opening of the insulative body to the flanged bore of the contact component, the insulative bore being formed around the second pin and having a perimeter surface flush with the perimeter surface of the flanged bore.

3. The method of claim 2, wherein the second pin includes a protrusion along a profile thereof to create a groove about a perimeter of the insulative bore that is formed around the second pin, the groove being located in proximity to the opening at the outer surface of the insulative body.

4. The method of claim 1, wherein the mold comprises core mold, and the injecting of the insulative material comprises injecting a first shot of an insulative material to form a core portion of the insulative body, and further comprising:
   positioning the flanged bore of the contact component around a third pin in an overlay mold, after injecting the first shot of insulative material, a perimeter surface of the positioned flanged bore being a minimum slip fit clearance fit around the third pin to create a shutoff; and
   forming an overlay portion of the insulative body by injecting a second shot of an insulative material around the contact component, the first and third pins, and the core portion of the insulative body in the overlay mold, the overlay portion including an opening located at an outer surface thereof and an insulative bore that extends from the opening of the overlay portion to the flanged bore of the contact component, the opening and the insulative bore of the overlay portion being formed around the third pin, and the insulative bore having a perimeter surface flush with the perimeter surface of the flanged bore of the contact component.

5. A method for forming a connector module assembly for an implantable medical device, the method comprising:
- positioning a core pin in a connector bore of each of a plurality of contact components;
- mounting the plurality of contact components, each with the corresponding core pin positioned therein, in a welding fixture along with an electrical component, such that each of a plurality of elongate finger-like portions of the electrical component is located in proximity to a corresponding contact component for welding;
- welding each mounted contact component to the corresponding elongate finger-like portion of the electrical component in proximity therewith;
- positioning a flanged bore of each of the plurality of welded contact components around a corresponding pin in a mold, each flanged bore being in fluid communication with the corresponding connector bore, and a perimeter surface of each positioned flanged bore being a minimum slip-fit clearance fit around the corresponding pin to create a shutoff; and
- forming an insulative body of the connector module assembly by injecting an insulative material around the plurality of welded contact components, the electrical component, the core pins, and the pins in the mold, the insulative body including an opening formed around each pin and located at an outer surface of the insulative body, for passage into the flanged bore of each contact component.

6. The method of claim 5, wherein mounting the plurality of contact components in the welding fixture comprises positioning the flanged bore of each contact component around a corresponding fixture pin, the perimeter surface of each flanged bore being a minimum slip-fit clearance fit around the corresponding fixture pin.

7. The method of claim 5, wherein the mold comprises core mold, and the injecting of the insulative material comprises injecting a first shot of an insulative material to form a core portion of the insulative body, and further comprising:
- positioning the flanged bore of each of the plurality of contact components around a corresponding pin in an overlay mold, after injecting the first shot of insulative material, a perimeter surface of each positioned flanged bore being a minimum slip-fit clearance fit around the corresponding pin in the overlay mold to create a shut-off; and
- forming an overlay portion of the insulative body of the connector module assembly by injecting a second shot of insulative material around the plurality of contact components, the core portion, the core pins and the pins in the overlay mold, the overlay portion comprising a plurality of insulative bores, each insulative bore extending from a corresponding opening of the insulative body, at an outer surface of the overlay portion, to the flanged bore of the corresponding contact component, and each insulative bore being formed around the corresponding pin in the overlay mold and having perimeter surface flush with the perimeter surface of the corresponding flanged bore.

\* \* \* \* \*